(12) United States Patent
Loucaides

(10) Patent No.: US 8,911,793 B1
(45) Date of Patent: Dec. 16, 2014

(54) ALGISTATIC WATER TREATMENT SOLUTION AND METHOD OF MAKING

(76) Inventor: George Loucaides, Seven Hills, OH (US)

( * ) Notice: Subject to any disclaimer, the term of this patent is extended or adjusted under 35 U.S.C. 154(b) by 501 days.

(21) Appl. No.: 12/947,047

(22) Filed: Nov. 16, 2010

Related U.S. Application Data

(60) Provisional application No. 61/261,853, filed on Nov. 17, 2009.

(51) Int. Cl.
*A61K 33/34* (2006.01)
*A61K 33/38* (2006.01)
*A61K 31/194* (2006.01)

(52) U.S. Cl.
USPC ............ 424/630; 424/618; 424/638; 514/574

(58) Field of Classification Search
USPC ........................... 424/630, 638, 618; 514/574
See application file for complete search history.

(56) References Cited

U.S. PATENT DOCUMENTS

| | | |
|---|---|---|
| 4,263,114 A | 4/1981 | Shindell |
| 4,492,618 A | 1/1985 | Eder |
| 4,525,253 A | 6/1985 | Hayes |
| 4,680,114 A | 7/1987 | Hayes |
| 5,541,150 A | 7/1996 | Garris |
| 5,632,904 A | 5/1997 | Samad et al. |
| 6,093,422 A | 7/2000 | Denkewicz |
| 6,287,450 B1 | 9/2001 | Hradil |
| 6,387,415 B1 | 5/2002 | Garris |
| 6,949,184 B2 | 9/2005 | Ashton |
| 7,122,115 B2 | 10/2006 | Holt |
| 7,470,369 B2 | 12/2008 | Diallo |
| 7,485,259 B2 | 2/2009 | Eldred |

*Primary Examiner* — Sue Liu
*Assistant Examiner* — Nathan W Schlientz
(74) *Attorney, Agent, or Firm* — Fay Sharpe LLP

(57) ABSTRACT

Systems and methods are described that facilitate generating and storing a concentrated copper and silver ion solution for treating a remote water volume (e.g., a pool, fountain, hot tub, cooling tower, etc.), in accordance with various features described herein. Citric acid and a water-soluble binding polymer are added to a volume of water. The intermediate solution is circulated past an ion generator for a predetermined time period, and copper ions generated thereby are bound by the binding polymer and/or chelated by the citric acid. Once a desired concentration of copper ions has been achieved, the concentrated solution is stored in portable vessels for transport to the remote water volume. Concentrated solution is added to the remote water volume to achieve a concentration therein of approximately 0.2-0.3 ppm.

20 Claims, 4 Drawing Sheets

US 8,911,793 B1

ALGISTATIC WATER TREATMENT SOLUTION AND METHOD OF MAKING

The present application claims the benefit of U.S. Provisional Application No. 61/261,853, filed Nov. 17, 2009, which is incorporated herein by reference in its entirety.

BACKGROUND

The subject application relates to water treatment, and more particularly to generating a concentrated copper and silver ion-based water treatment solution off-site, storing the solution in portable containers, and treating remote water volumes with the solution.

Conventional water treatment systems and methods involve chlorine treatments. While generally cheap and easy to maintain, chlorine has many undesirable side effects. Chlorine is used in pesticides and can have detrimental effects on the environment, on health, and on industrial equipment.

Another popular water treatment method involves chlorine salt. This technique requires a generator to be installed on existing pool or fountain plumbing. An amount of diluted chlorine salt is periodically added to the water volume therein. As the chlorine salt circulates past the generator, the salt is separated from the chlorine to generate free chlorine that maintains water quality. The systems are typically expensive, and must be installed on site at the location of the water volume being treated.

Ozone and UV water treatment systems have been used to treat swimming pools and spas and the like, but these systems leave no residual water treatment agent in the water. Rather, only water that passes the ozone generator or UV source is treated. If water is not circulating past the ozone generator or UV source, then it does not get treated.

Metal ion generators have been used in swimming pools for ionic water maintenance. Typically, these systems are installed in the filtration system of a swimming pool or the like and are expensive to install and monitor.

Accordingly, there is an unmet need for systems and/or methods that facilitate providing a consistent, cost-effective, clean ion solution for treating remote water volumes while overcoming the aforementioned deficiencies.

BRIEF DESCRIPTION

In accordance with various aspects described herein, systems and methods are described that facilitate generating an algistatic solution for treating water volumes (e.g., pools, fountains, spas, etc.). For example, a method for generating a concentrated copper ion solution for treating a remote water volume comprises determining a plurality of solution parameters for the copper ion solution, the parameters including a target ion concentration for the solution, and adding citric acid to a predetermined volume of water to generate an intermediate solution. The method further includes adding a water-soluble binding agent, which binds free copper ions, to the intermediate solution, and circulating the intermediate solution past an ion generator for a predetermined amount of time in order to generate the concentrated copper ion solution having the target ion concentration. Optionally, the method includes one or more of distributing the solution to one or more storage vessels, transporting the solution to the remote water volume, and adding an amount of solution to the remote water volume to achieve approximately 0.2-0.3 ppm copper ion concentration therein.

According to another aspect, a method of generating an algistatic and bacteriostatic solution for treating a water volume comprises adding a predetermined volume of water to a tank, determining solution parameters including a final solution pH and a final solution copper ion concentration, adding a predetermined amount of citric acid to the water in the tank to generate an intermediate solution, and adding a predetermined amount of binding polymer to the intermediate solution. The method further comprises circulating the intermediate solution past a copper-ion-generating ionizer for a predetermined time period, determining the pH of the intermediate solution after the predetermined time period has elapsed, and, if the pH of the intermediate solution is less than a predetermined pH level, adding a solute that raises the pH of the intermediate solution to at least the predetermined pH level. Additionally the method comprises iteratively adding citric acid and binding polymer to the intermediate solution, circulating the intermediate solution past the ionizer, and adjusting pH to maintain the intermediate solution at an approximately neutral pH, until a final solution is generated having the final solution pH and the final solution copper ion concentration specified by the solution parameters.

DETAILED DESCRIPTION

In accordance with various features described herein, systems and methods are described that facilitate generating a copper and silver based algistatic and bacteriostatic solution for treating water volumes (e.g., pools, Jacuzzis/hot tubs/spas, fountains, cooling tower water tanks, closed loop boiler systems, and the like). For example, the solution is generated to have a concentration of approximately 30 ppm to 300 ppm or more of copper ions, is stored until needed, and is subsequently added to a water volume to achieve a concentration therein of approximately 0.2-0.3 ppm to prevent plant growth (e.g., algae or the like). An advantage of the solution over conventional approaches is that the herein-described solution does not contain or use copper sulfate, which is corrosive and reduces free copper concentrations. Another advantage is that the herein-described solution can be generated at concentrations not previously available, which reduces an amount of solution that needs to be stored and/or applied to a water volume to achieve a desired target concentration therein (e.g., 0.2-0.3 ppm or so). Another advantage is that the high-concentration solution mitigates a need for expensive in-situ ion-generating systems for water maintenance, which require constant monitoring.

"Water volume" as used herein refers to a swimming pool, hot tub, cooling tower reservoir, fountain, or any other suitable water volume for which it is desirable to prevent or arrest bacterial or plant growth.

Figure 1:
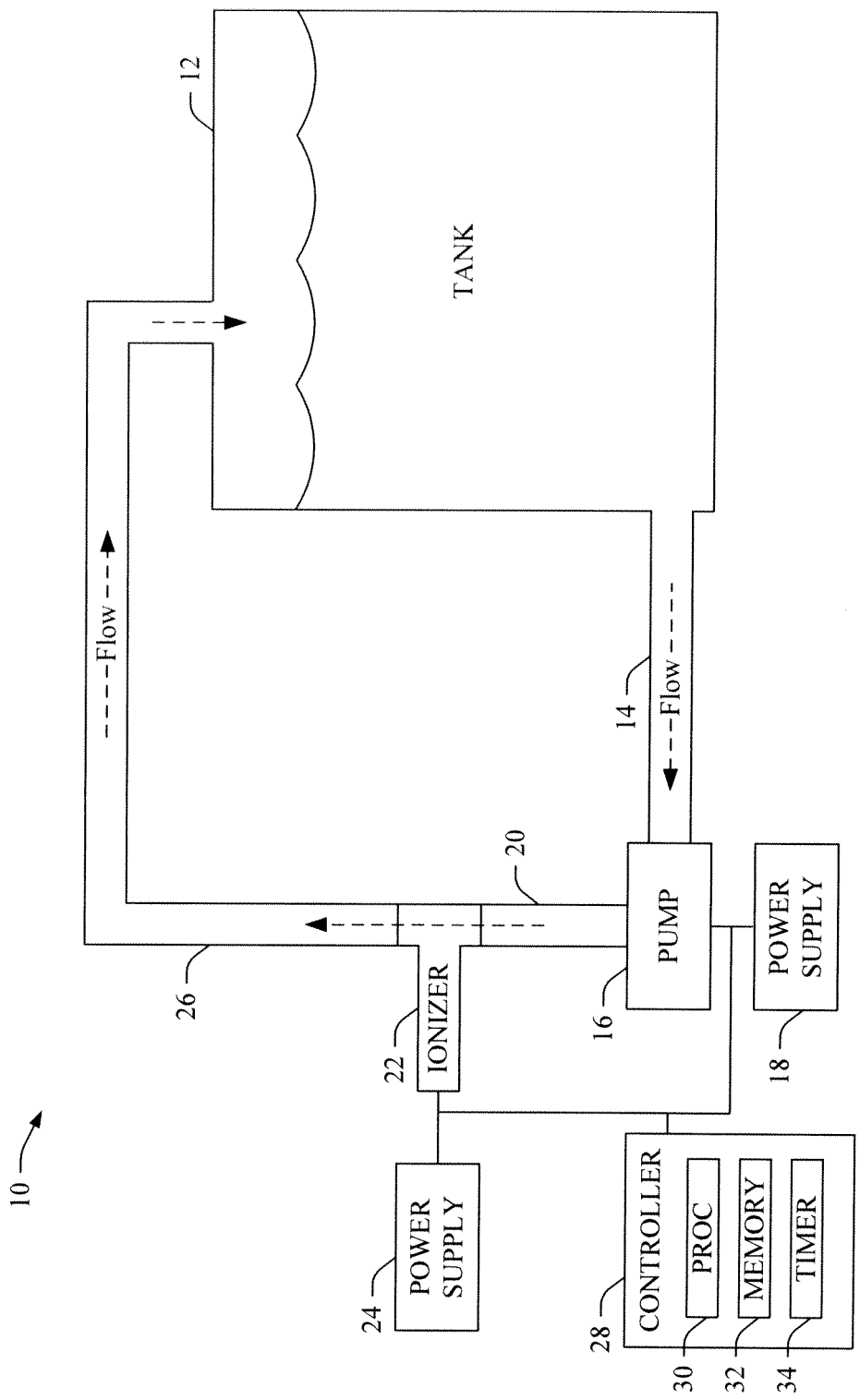
FIG. 1 illustrates a system that facilitates generating the here-described copper solution having sequestered copper of a desired predetermined concentration, in accordance with various aspects.

With reference to FIG. 1, a system 10 is illustrated that facilitates generating the here-described copper solution having sequestered copper of a desired predetermined concentration, in accordance with various aspects. Once the desired concentration is achieved, the solution is bottled or otherwise stored for transportation to a water volume to be treated. The system 10 includes a tank or reservoir 12 in which the solution is generated, and which is coupled by a first conduit 14 to a pump 16. The tank may be made of plastic, glass, PVC, stainless steel, or any other suitable non-reactive material. The pump is coupled to a power supply 18 that provides power to the pump, causing the pump to draw fluid from the tank 12 and force the fluid through a second conduit 20 to an ion generator 22 or "ionizer" that generates copper ions in the fluid. The ionizer 22 is coupled to a power supply 24 by each of a positive and negative lead (see FIG. 2), which apply a voltage across a metal alloy bar inside the ionizer to generate the copper ions. The fluid flows past or through the ionizer 22 into a third conduit 26, which returns the fluid to the tank 12.

According to an example, the pump 16 is a centrifugal pump or the like and has a flow rate in the range of approximately 1-50 gpm, although other flow rates are envisioned as a function of water volume, tank size, etc. The conduits 14, 20, 26 are PVC pipes or the like, having an interior diameter of approximately 2 inches. The ionizer 22 is a metal ion generator, such as is described in U.S. Pat. No. 6,949,184, which is hereby incorporated by reference in its entirety. For instance, the ionizer in this example is a single-bar copper-silver ion generator. However, it will be understood that dual-bar ionizers may be used in conjunction with the various systems and methods described herein. Furthermore, other metals beyond copper and silver may be employed in the ionizers, as is known in the art.

Power supplies 18 and 24 are variable power supplies. The tank is a 100 gallon tank, or any other suitable size tank. It will be appreciated that the foregoing components, properties, and tank volume are provided by way of example only, and that the herein-described systems and methods are not limited thereto. For instance, the pump and/or ionizer may be any suitable pump and/or ionizer, and their corresponding power supplies may be selected according to their respective power needs. Additionally, the conduits may be silastic tubing, stainless steel, or any other suitable, non-reactive material, and may have any desired or suitable interior diameter.

Additionally, the system 10 comprises a controller 28, which in turn comprises a processor 30, a memory 32, and a timer 34. The memory stores, and the processor executes, computer- or machine-executable instructions for performing one or more functions and/or acts described herein. In one embodiment, the controller is an interface into which a user enters information such as a desired number of pump and/or ionizer cycles, durations thereof, duty cycle information, etc. For instance, the user may enter a cycle duration of 8 hours, a duty cycle of 0.75, and a cycle number of 2 for the pump, so that the controller causes the power supply 18 to provide power to the pump 16 for 6 hours and then power down for 2 hours before providing power for another 6 hours. In this example, the controller 28 employs the timer 34 (or a counter or the like) to determine when to signal the power supply 18 to turn on and shut off. A user may control the power supply 24 for the ionizer 22 in a similar manner, using the controller.

In another example, the user enters solution parameter information (e.g., initial pH, TDS levels, approximate ionizer bar residual (e.g., amount of original ionizer bar left remaining after repeated use) information, water volume, and the like), and the processor 30 executes instructions stored in the memory 32 to determine an appropriate run time (e.g., number and duration of cycles or a continuous run period, duty cycle, amount of water-soluble binding polymer and/or sequestering agent to be added to the water, etc.) to generate the target ion concentration. According to one aspect, the processor executes a table lookup on a lookup table stored in the memory 32 to identify an appropriate run time and/or polymer and sequestering agent amounts for generating the target concentration given the user-entered solution parameters.

In yet another example, the controller includes a graphical user interface (not shown) by which the user enters solution parameters and/or monitors the process of generating the solution.

Figure 2:
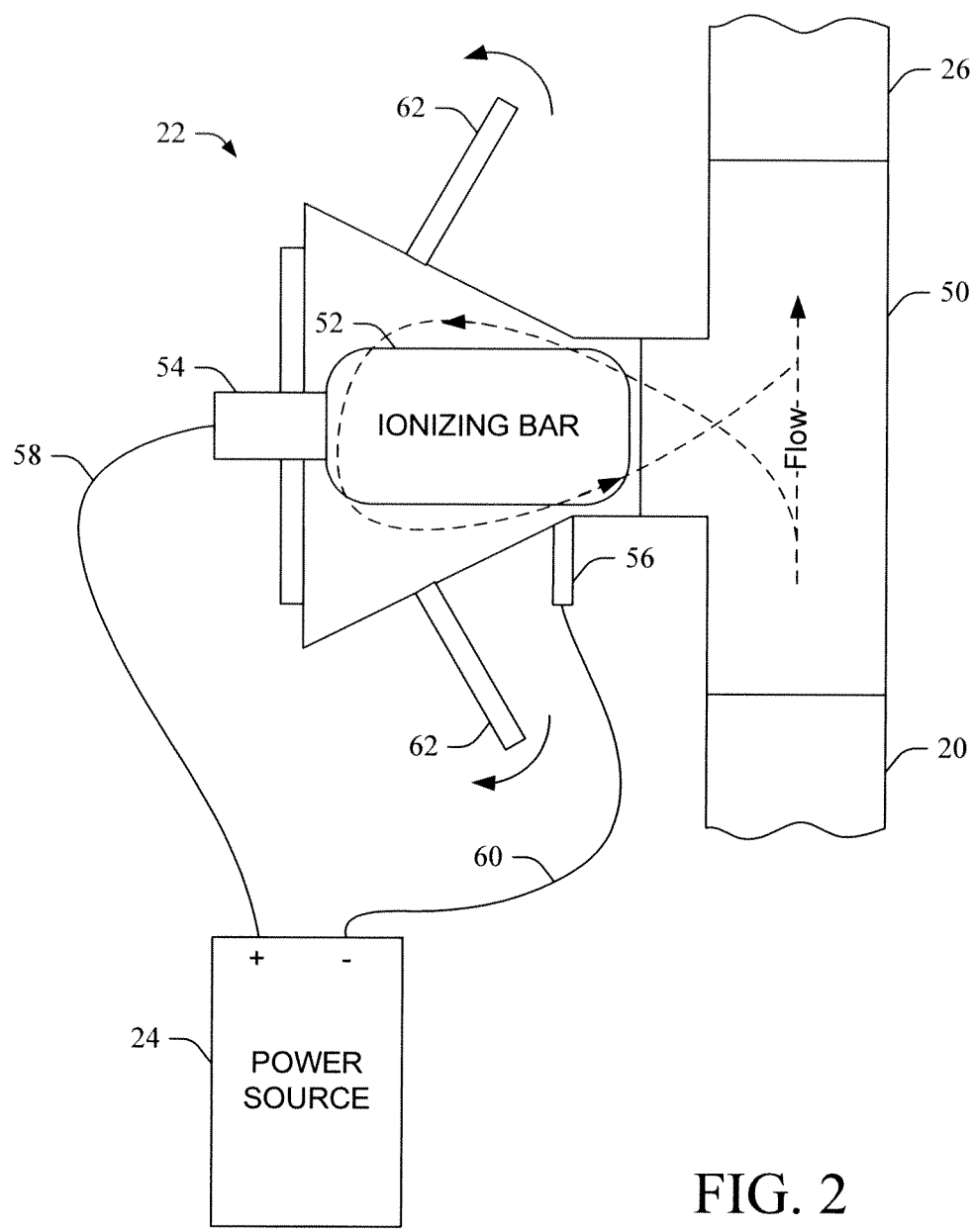
FIG. 2 illustrates an example of an ionizer such as may be used in conjunction with the systems and methods described herein.

FIG. 2 illustrates an example of an ionizer 22 such as may be used in conjunction with the systems and methods described herein. The ionizer may be an ion generator such as is described in U.S. Pat. No. 6,949,184, or any other suitable ion generator. The ionizer 22 is coupled to a T-fitting 50 (e.g., PVC or the like), which is further coupled to the conduit 20 and the conduit 26. Fluid flows through the conduit 20 into the T-fitting 50 and past an ionizing bar 52 in the ionizer 22 before exiting the T-fitting 50 into the conduit 26.

Flow direction is managed by the pump 16 (FIG. 1). A positive terminal 54 and a negative terminal 56 are positioned across the ionizing bar 52 to generate potential there across upon activation of the power source 24. The positive terminal 54 is coupled to a corresponding positive terminal (indicated by a "+") on the power source 24 by a lead 58, and the negative terminal 56 is coupled to a corresponding negative terminal (indicated by a "−") on the power source 24 by a lead 60. The power source may be, for instance, a deep cycle battery, an AC/DC converter that converts AC electrical current from a wall outlet to DC current, a variable DC power supply, or any suitable DC power source. A pair of clamp levers 62 are illustrated that, when moved outward from the ionizer 22, cause the ionizer to lock into position in the T-fitting 50.

In one example, the ionizing bar 52 is a copper-silver ionizing bar that produces copper (and silver) ions that are bound by a water-soluble binding agent (e.g., an anionic or cationic polymer added to the tank) and/or chelated by an acid (e.g., citric acid or the like). The ionizer bar, according to one example, comprises approximately 90% copper and 10% silver, such that ions are released into the solution in a 9:1 copper:silver ratio when voltage is applied across the ionizer bar. For instance, if a target copper ion concentration for algistatic water treatment is 180 ppm, then such a solution will also contain approximately 20 ppm silver ions, which aid in controlling bacteria in a water volume to which the solution is applied. However, it will be appreciated that the ionizer bar may comprise any ratio (e.g., 80:20, 50:50, 95:5, etc.) of copper and silver to achieve a desired ratio of copper to silver ions in the solution.

Figure 3:
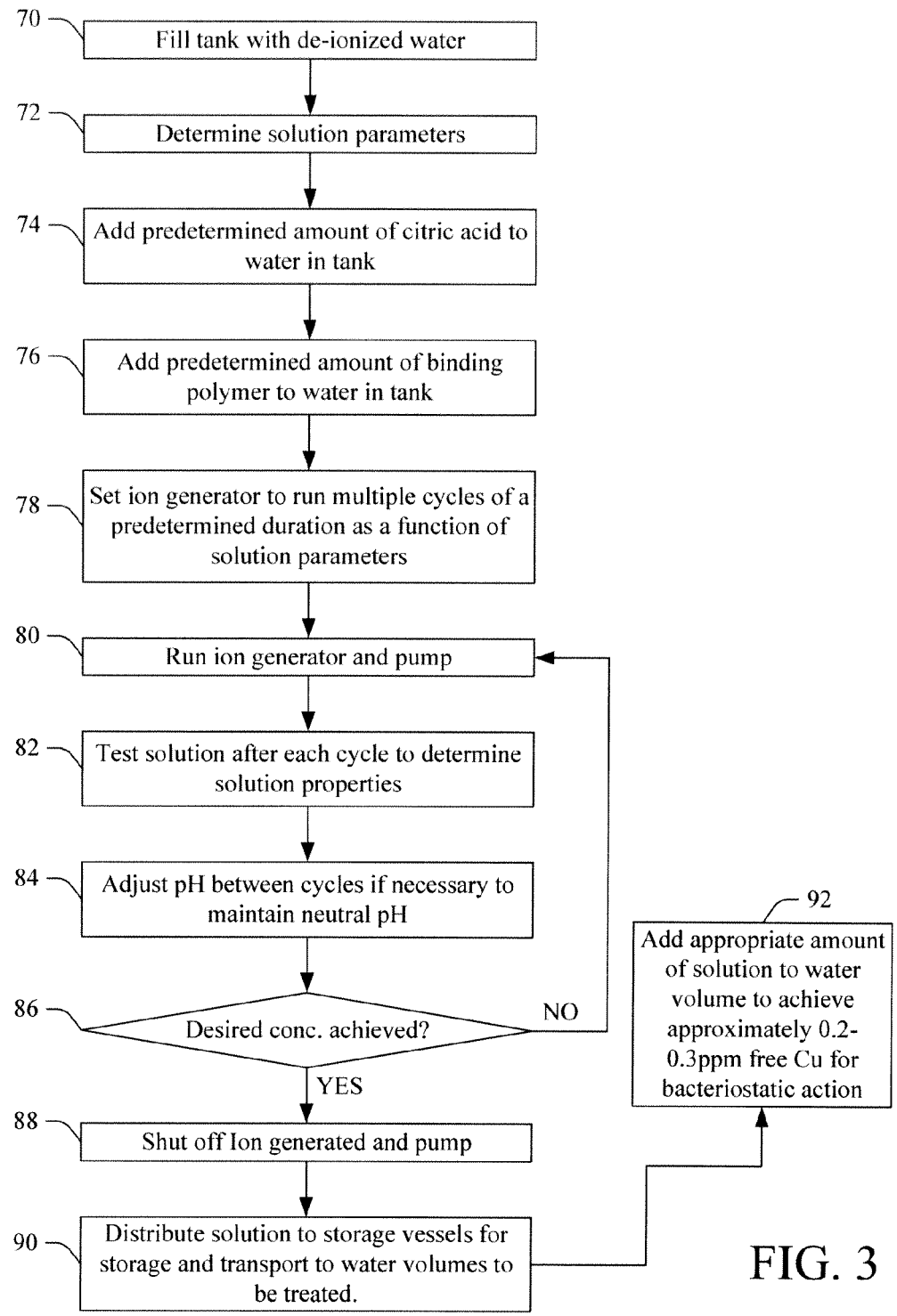
FIG. 3 is an illustration of a method of generating an algistatic solution for treating a water volume, in accordance with one or more aspects described herein.
Figure 4:
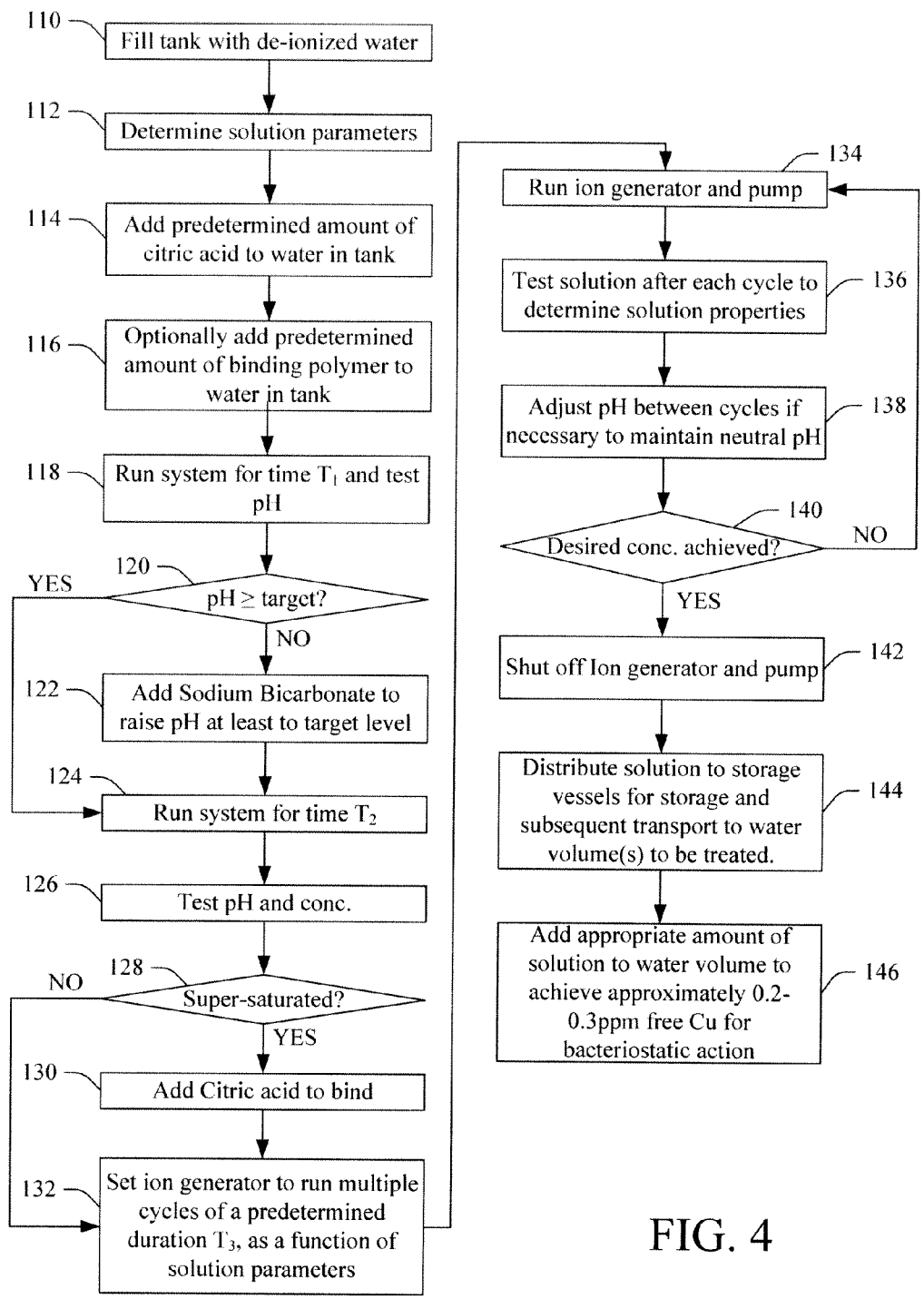
FIG. 4 is an illustration of a method of generating an algistatic solution for treating a water volume, in accordance with one or more aspects described herein.

FIGS. 3-4 illustrate one or more methods related to algistatic solution generation and water treatment, in accordance with various features. While the methods are described as a series of acts, it will be understood that not all acts may be required to achieve the described goals and/or outcomes, and that some acts may, in accordance with certain aspects, be performed in an order different that the specific orders described.

FIG. 3 is an illustration of a method of generating an algistatic solution for treating a water volume, in accordance with one or more aspects described herein. At 70, a predetermined volume of water is added to a tank. The water may be filtered water, de-ionized water, or both filtered and de-ionized. Filtering the water facilitates removal of dissolved solids and chlorine that may be present in tap water or the like. At 72, solution parameters are determined. Solution parameters may include, without being limited to, target copper ion concentration, water pH before and/or after solute addition, total dissolved solids (TDS) level before and/or after solute addition, system (e.g., pump and ion generator) run time, system cycle number and duration, duty cycle, residual ion bar material, etc. At 74, a predetermined amount of chelating agent (e.g., citric acid) is added to the water in the tank, to generate an intermediate solution. At 76, a predetermined amount of water-soluble binding polymer is added to the intermediate solution in the tank. At 78, the ion generator is programmed to run a predetermined number of cycles of a given duration as a function of the solution parameters. For instance, given a desired target solution ion concentration, at a given water pH and TDS level, and given the known volumes of water, citric acid, and binding polymer, a table lookup can be performed to identify a number of cycles of a given duration (e.g., total run time of the system) to achieve the desired ion concentration. At 80, the ion generator and pump are powered on. It will be appreciated that the pump is in an ON state whenever the ion generator is ON. When the ion generator is in an OFF state, the pump may be in either of an ON or OFF state.

At 82, the solution in the tank is tested to determine solution properties (e.g., pH, TDS level, ion concentration, etc.). In one example, the intermediate solution is tested after each cycle of the ionizer. At 84, pH is adjusted between ionizer cycles if necessary to maintain a neutral pH in the intermediate solution. At 86, a determination is made regarding whether the desired target concentration of copper ions has been reached. If not, the method reverts to 80 for continued ion generation. If the target concentration has been achieved, then at 88, the ion generator and pump are shut off. At 90, concentrated copper ion solution is transferred from the tank to storage vessels (e.g., bottles, jugs, or the like). For example, the solution may be stored in 5-gallon bottles, 1-gallon bottles, 1-liter bottles, etc., for treating larger water volumes (e.g., pools and/or fountains), or in smaller bottles (e.g., on the order of ounces or milliliters) for treating smaller water volumes (e.g., spas or hot tubs, small ponds or aquariums, etc.).

Optionally, at 92, the stored solution is added to a water volume (e.g., a pool, fountain, cooling tower, spa, etc.) in an appropriate volume to achieve approximately 0.2-0.3 ppm copper ions in the water volume. For instance, if the solution is generated to have a target concentration of 90 ppm copper ions, and a spa has a volume of 300 gallons, then approximately 0.6-1.0 gallons of solution can be added to the spa to achieve a 0.2-0.3 ppm copper ion concentration in the spa water.

According to an example, the predetermined volume of water added to the tank at 70 is approximately 100 gallons of filtered water or de-ionized water. As for the solution parameters measured at 72, the pH may be between approximately 4 and approximately 9, with adjustments being made as necessary. Total Dissolved Solids (TDS) levels are in a range between 100 ppm to 2500 ppm. Various metals may be used for ion generation through electrolysis, including without being limited to copper, zinc, silver, and brass. A variety of different ion generators may be used, such as the ion generator described in U.S. Pat. No. 6,949,184. As illustrated in FIG. 1, the system setup includes the tank 12, ion generator 22 with power supply 24, water moving pump 16 and power supply 18, and various plumbing and valves. At 74, approximately 75 grams of citric acid is added to tank to generate the intermediate solution. At 76, approximately 40 ml of cationic or anionic polymer is added to the intermediate solution. At 78, the ion generator is set or programmed for 2 to 20 cycles of six hours on and two hours off depending on the solution parameters (e.g., target ion concentration, copper ionizer bar residual, water contaminants, and other variables). Voltage across the ionizer bar may range between 4 to 31 volts and 0.1 to 3 amps. After each cycle solution is tested for concentration, TDS and pH with adjustments being made accordingly to maintain a neutral pH. The system is then run until the desired ion concentration is achieved.

According to another example, citric acid is added to a volume of water in the tank, which is being circulated past the ionizer by the pump, in order to chelate the copper ions generated by the ionizer. As the citric acid reduces the pH of the solution, a base (e.g., soda ash, sodium bicarbonate, or some other suitable "pH up" additive) is added to the solution to bring the solution back up into a neutral range (e.g., 7.0-8.0 or so). This process is repeated periodically e.g., every 24-48 hours or so) while solution is continuously circulated through the system. The addition of citric acid and corresponding pH correction using the basic additive is iterated several times (e.g., 2-5 times in one example), and each iteration achieves an incremental copper ion concentration increase. For instance, after the first iteration, the solution may have a concentration of approximately 50 ppm. After the second iteration, the concentration may be approximately 100 ppm. After the fifth iteration, the concentration may be approximately 250 ppm, at which time the process may be terminated and the solution may be bottled or stored for transportation to a water volume to be treated.

FIG. 4 is an illustration of a method of generating an algistatic and bacteriostatic solution for treating a water volume, in accordance with one or more aspects described herein. At 110, a predetermined volume of water is added to a tank. The water may be filtered water, de-ionized water, or both filtered and de-ionized. At 112, solution parameters are determined. Solution parameters may include, without being limited to, target copper ion concentration, water pH before and/or after solute addition, total dissolved solids (TDS) level before and/or after solute addition, system (e.g., pump and ion generator) run time, system cycle number and duration, duty cycle, residual ion bar material, etc. At 114, a predetermined amount of citric acid is added to the water in the tank to generate an intermediate solution. At 116, a predetermined amount of water-soluble binding polymer is added to the intermediate solution in the tank. The binding polymer attracts the free copper ions and binds so that they do not bind with chlorides that may be present in the water volume to be treated. That is chlorides are present in tap water, which is typically used to fill a pool, Jacuzzi, cooling tower, or other water volume to be treated. Additionally, debris or mineral material found in the tap water may have an affinity for copper. By binding the copper ions to the binding polymer, the copper is discouraged from binding with anything else that may cause staining and/or bring the copper out of its ionic state.

At 118, the system (e.g., ionizer and pump) are run for a predetermined period $T_1$, and pH is tested thereafter. At 120, a determination is made regarding whether the solution pH is greater than or equal to a target or desired pH (e.g., a neutral pH of 6.5-7 or so). If the measured pH is less than the target or desired pH, then at 122 an appropriate amount of sodium bicarbonate is added to the intermediate solution to bring the pH to a neutral level (e.g., approximately 7). At 124, the system is then powered on again and run for a predetermined time period $T_2$.

If, at 120, it is determined that the intermediate solution pH is greater than or equal to the target or desired pH, then the method proceeds directly to 124. At 126, intermediate solution pH and copper ion concentration are tested. At 128, a determination is made regarding whether the intermediate solution is super saturated (e.g., whether copper is falling out of solution in the tank), which may be performed by visual inspection of the solution in the tank. If so, the citric acid is added to the solution to chelate the extra copper ions and keep them in solution, at 130. At 132, the ionizer and pump are set to run multiple cycles of a predetermined duration $T_3$, with a predetermined duty cycle (e.g., 75%), as a function of the solution parameters identified at 116. For instance, the system may be programmed to run for several cycles of a predetermined duration $T_3$ with intermittent OFF periods (e.g., ON 5-6 hours, OFF 1-2 hours, etc.). If the determination at 128 indicates that the intermediate solution is not super saturated, then the method proceeds directly to 132.

At 134, the pump and ionizer are run according to the programmed settings. At 136, solution is tested after each cycle to evaluate solution properties (e.g., pH, ion concentration, IDS levels, etc.). At 138, pH is adjusted between cycles to maintain a neutral pH, if necessary. At 140, a determination is made regarding whether the desired or target ion concentration has been achieved. If not, the method reverts to 134 for continued ion generation. If the target concentration has been achieved, then at 142, the ion generator and pump are shut off. At 144, concentrated copper ion solution is transferred from the tank to storage vessels (e.g., bottles, jugs, or the like). For example, the solution may be stored in 5-gallon bottles, 1-gallon bottles, etc., for treating larger water volumes (e.g., pools and/or fountains), or in smaller bottles (e.g., on the order of ounces or liters) for treating smaller water volumes.

Optionally, at 146, the stored solution is added to a water volume (e.g., a pool, fountain, cooling tower, spa, etc.) in an appropriate volume to achieve approximately 0.2-0.3 ppm copper ions in the water volume. For instance, if the solution is generated to have a target concentration of 200 ppm copper ions, and a spa has a volume of 400 gallons, then approximately 0.4-0.6 gallons of solution can be added to the spa to achieve a 0.2-0.3 ppm copper ion concentration in the spa water.

According to an example, the predetermined volume of water added to the tank at 110 is approximately 100 gallons of filtered water or de-ionized water. As for the solution parameters measured at 112, the pH may be between approximately 4 and approximately 9, with adjustments being made as necessary. Total Dissolved Solids (TDS) levels are in a range between 100 ppm to 2500 ppm. Various metals may be used for ion generation through electrolysis, including without being limited to copper, zinc, silver, and brass. A variety of different ion generators may be used, such as the ion generator described in U.S. Pat. No. 6,949,184. As illustrated in FIG. 1, the system setup includes the tank 12, ion generator 22 with power supply 24, water moving pump 16 and power supply 18, and various plumbing and valves. At 114, approximately 75 grams of citric acid is added to the tank to generate the intermediate solution. Optionally, 40 ml of a cationic or anionic binding polymer is added at 116. The intermediate solution is then circulated for one hour and pH is then tested, at 118. If pH is between approximately 3.5 and approximately 6.5, then 100 grams of sodium bicarbonate is added to raise the pH to above 7.0, at 122. The intermediate solution is then turned on to generate ions. After several ion generating cycles, the solution is tested for pH and copper levels, at 126. If the intermediate solution shows signs of super saturation (e.g., copper falling out of solution), an additional 75 grams of citric acid is added, at 130. The ion generator is programmed for 2 to 20 cycles of six hours on and two hours off, depending on target ion concentration, copper bar residual and water contaminants, and other variables. Voltage across the ionizer bar may range between 4 to 31 volts, and 0.1 to 3 amps may be applied to the ionizer bar. After each cycle, the intermediate solution is tested for ion concentration, TDS, and pH, with adjustments being made accordingly to maintain a neutral pH. Upon achieving the desired ion concentration, the system is powered off and the concentrated copper ion solution is stored in storage vessels (e.g., jugs, bottles, etc.).

It will be appreciated that the various volumes and amounts (e.g., 100 gallons, 75 grams of citric acid, 40 ml of binding polymer), described in the examples provided herein are illustrative in nature and that the herein-described innovation is not limited to these amounts, values, volumes, etc. Rather any suitable initial water volume can be employed in conjunction with the described systems and methods, with the amounts of solutes, run times, etc., being adjusted accordingly.

With regard to the binding polymer described in steps 76 and 116 of respective FIGS. 3 and 4, according to one example the binding polymer is Jack's Magic, The Ionizer Stuff, which is available off-the-shelf at pool supply stores. Examples of suitable binding agents include anionic polymers such as polyacrylic acid, polymethacrylic acid, polymaleic acid, polyaspartic acid, copolymers, terpolymers, tetrapolymers thereof and/or the sodium, potassium, and/or calcium salts of such polymers. Examples of suitable cationic polymers include poly[oxyethylene-(dimethylimino) ethylene-(dimethylimino) ethylene dichloride], polyvinyl amine, chitosan, polyethylene amine or a polymer of 1,6-hexanediamine-N,N,N',N'-tetramethyl or the fluoride or chloride salts thereof. Other examples include poly(allylamine hydrochloride), poly(acrylic acid sodium salt), and the like.

The methods of FIGS. 3 and 4 have been described with regard to a binding polymer (e.g., Jack's Magic) and a sequestering agent (e.g., citric acid), however, other sequestering agents may be employed. For instance, conventional organic sequestering agents can be used with the polymeric binding agent. Such sequestering agents may include without being limited to, hydroxy-carboxylic acids, aminocarboxylic acids, polyamines, alkanolamines, polyphosphates, phosphonic acids, crown ethers, amino acids, etc. Other examples of suitable organic acids include oxalic acid, suberic acid, acetic acid, tricarballic acid, succinic acid, malonic acid and maleic acid, and the salts thereof. Still other examples include hydroxy-carboxylic acids such as citric acid, gluconic acid, tartronic acid, lactic acid, tartaric acid, malic acid, glyceric acid, or tetrahydroxy succinic acid, and variants of the foregoing.

The following examples of solution parameters and system run times are provided for illustrative purposes. In one example, the initial pH of the water is approximately 7, the water volume is approximately 65 gallons, the ionizer bar residual is 100% (i.e., the bar is new), TDS levels are between 800 and 1000, and desired or target copper ion concentration is approximately 30 ppm. In this case, the power supply for the ion generator is set to approximately 8-11V at 0.3-0.6 amps, and the system is run for approximately 10-16 hours. The run time may be divided into cycles (e.g., two cycles of 5-8 hours each with 0-2 hours between cycles), or may be continuous. Appropriate amounts of water-soluble binding polymer (e.g., 2-4 ounces) are added to the solution prior to run time. pH is maintained at approximately 7 by adding acid or soda as needed.

According to another example, the target concentration is approximately 70 ppm, the water volume is approximately 65 gallons, initial pH is approximately 7, TDS is in the range of 700-800, and the ionizer bar is at approximately 80%. In this case, approximately 4 oz. of binding polymer and approximately 8 oz. of citric acid are added to the water volume prior to run time. The system is then run for approximately 10-12 hours at a voltage of approximately 8-9 volts and amperage of approximately 0.4-0.5 amps. pH is maintained at approximately 7 by adding acid or soda as needed.

According to another example, the target concentration is approximately 100 ppm, initial pH is approximately 7, the water volume is approximately 65 gallons, TDS is in the range of 700-800, and the ionizer bar is at approximately 80%. In this case, approximately 4 oz. of binding polymer and approximately 8 oz. of citric acid are added to the water volume prior to run time. The system is then run for approximately 10-12 hours at a voltage of approximately 19-20 volts and amperage of approximately 0.7-0.9 amps. pH is maintained at approximately 7 by adding acid or soda as needed.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method of generating a concentrated copper ion solution for treating a remote water volume, comprising:
    determining a plurality of solution parameters for the copper ion solution, the parameters including a target ion concentration for the solution;
    adding citric acid to a predetermined volume of water to generate an intermediate solution;
    adding a water-soluble binding agent, which binds free copper ions, to the intermediate solution;
    circulating the intermediate solution past an ion generator for a predetermined amount of time in order to generate the concentrated copper ion solution having the target ion concentration; and
    distributing the concentrated copper ion solution to one or more storage vessels for transport to the remote water volume;
    wherein the concentrated copper ion solution does not contain copper sulfate.

2. The method according to claim 1, wherein the water volume is located in one of a swimming pool, a spa or Jacuzzi, a fountain, and a cooling tower.

3. The method according to claim 2, wherein the water volume is located remotely from a site at which the solution is generated.

4. The method according to claim 1, wherein the binding agent is a water-soluble anionic binding polymer, and wherein the citric acid chelates molecules of the binding agent, having copper ions bound thereto, in order to increase the concentration of copper ions in solution.

5. The method according to claim 1, wherein the binding agent is a water-soluble cationic binding polymer, and wherein the citric acid chelates molecules of the binding agent, having copper ions bound thereto, in order to increase the concentration of copper ions in solution.

6. The method according to claim 1, wherein the ion generator is a single-bar copper-silver-ion generating ionizer.

7. The method according to claim 6, further comprising employing a copper-silver ionizer bar in the ionizer, the ionizer bar comprising approximately 90% copper and approximately 10% silver, wherein the concentrated copper ion solution also includes silver ions.

8. The method according to claim 1, further comprising treating the remote water volume by adding an amount of concentrated copper ion solution to achieve a concentration of 0.2-0.3 ppm copper ions in the remote water volume.

9. The method according to claim 1, wherein the target ion concentration is approximately 30 ppm to approximately 500 ppm.

10. The method according to claim 1, wherein the target ion concentration is approximately 200 ppm to approximately 300 ppm.

11. The method according to claim 1, further comprising adding approximately 30-60 ml of binding agent per 100 gallons of water when forming the intermediate solution.

12. The method according to claim 1, further comprising adding approximately 60-90 g of citric acid per 100 gallons of water when forming the intermediate solution.

13. The method according to claim 1, further comprising circulating the intermediate solution past the ion generator for approximately 10-16 hours.

14. The method according to claim 1, further comprising maintaining a neutral pH in the intermediate solution until the target ion concentration is achieved.

15. The method according to claim 1, further comprising applying a voltage of approximately 4V-30V across the ionizer to generate copper and silver ions in the intermediate solution.

16. The method of claim 1, wherein the predetermined volume of water is at least one of filtered water and de-ionized water.

17. The method according to claim 1, wherein the ionizer is a copper-ion generating ionizer.

18. A method of generating an algistatic and bacteriostatic solution for treating a water volume, comprising:
    adding a predetermined volume of water to a tank;
    determining solution parameters including a final solution pH and a final solution copper ion concentration;
    adding a predetermined amount of citric acid to the water in the tank to generate an intermediate solution;
    adding a predetermined amount of binding polymer to the intermediate solution;
    circulating the intermediate solution past a copper-ion-generating ionizer for a predetermined time period;
    determining the pH of the intermediate solution after the predetermined time period has elapsed;
    if the pH of the intermediate solution is less than a predetermined pH level, adding a solute that raises the pH of the intermediate solution to at least the predetermined pH level; and
    iteratively adding citric acid and binding polymer to the intermediate solution, circulating the intermediate solution past the ionizer, and adjusting pH to maintain the intermediate solution at an approximately neutral pH, until a final solution is generated having the final solution pH and the final solution copper ion concentration specified by the solution parameters.

19. The method of claim 18, wherein the final solution copper ion concentration is in the range of 200 ppm-300 ppm, and wherein the final solution pH is in the range of 6.0-8.0.

20. The method of claim 18, further comprising adding the final solution to a remote water volume in an amount that achieves a concentration of approximately 0.3 ppm copper ions in the remote water volume.

* * * * *